(12) United States Patent
Lee

(10) Patent No.: US 9,572,567 B2
(45) Date of Patent: Feb. 21, 2017

(54) MEDICAL CLIP, CLIP UNIT AND CLIP DEVICE

(76) Inventor: Se-dong Lee, Goyang-si (KR)

( * ) Notice: Subject to any disclaimer, the term of this patent is extended or adjusted under 35 U.S.C. 154(b) by 185 days.

(21) Appl. No.: 14/373,135

(22) PCT Filed: Jan. 18, 2012

(86) PCT No.: PCT/KR2012/000427
§ 371 (c)(1),
(2), (4) Date: Jul. 18, 2014

(87) PCT Pub. No.: WO2013/108940
PCT Pub. Date: Jul. 25, 2013

(65) Prior Publication Data
US 2014/0343581 A1 Nov. 20, 2014

(51) Int. Cl.
*A61B 17/08* (2006.01)
*A61B 17/04* (2006.01)
*A61B 17/10* (2006.01)
*A61B 17/122* (2006.01)

(52) U.S. Cl.
CPC ......... *A61B 17/0487* (2013.01); *A61B 17/083* (2013.01); *A61B 17/10* (2013.01); *A61B 17/122* (2013.01)

(58) Field of Classification Search
CPC .............. A61B 17/122; A61B 17/1285; A61B 17/1227; A61B 2017/0641; A61B 17/0487; A61B 17/064; A61B 17/0682; A61B 17/08; A61B 1/0014

USPC ....... 606/139, 142, 143, 151, 157, 158, 167, 606/205; 227/901, 902
See application file for complete search history.

(56) References Cited

U.S. PATENT DOCUMENTS

2010/0049217 A1 2/2010 Matsuoka et al.
2012/0116419 A1* 5/2012 Sigmon, Jr. ........ A61B 17/1285
606/142

FOREIGN PATENT DOCUMENTS

JP 2008-113673 A 5/2008
JP 2009-240757 A 10/2009
KR 10-2006-0123526 A 12/2006
KR 10-2010-0090987 A 8/2010

* cited by examiner

*Primary Examiner* — Katherine M Shi
(74) *Attorney, Agent, or Firm* — Novick, Kim & Lee, PLLC; Jae Youn Kim

(57) ABSTRACT

The present invention relates to a medical clip, a clip unit, and a clip device by which accuracy in access to a target (a site to be treated) can be secured and also which can be employed to suture or remove a site involving widespread tissue injury. As one example to achieve this, the present invention provides a medical clip including: a first arm and a second arm between which a target is placed and which together squeeze the target; a ring configured to connect one end of the first arm with one end of the second arm; a first ancillary arm articulated with the other end of the first arm; and a second ancillary arm articulated with the other end of the second arm.

10 Claims, 18 Drawing Sheets

MEDICAL CLIP, CLIP UNIT AND CLIP DEVICE

TECHNICAL FIELD

The present invention relates to a medical clip, a clip unit and a clip device, and more particularly, to a medical clip, a clip unit, and a clip device used for suturing or removing tissue in endoscopic surgery.

BACKGROUND ART

As a unit for suturing a wound site (hereafter, referred to as "wound"), for example, a technique for suturing wound by a clip unit operated by being inserted into a treatment instrument insertion channel for endoscope is known in the art as disclosed in Korean Patent No. 10-0815378.

In general, a clip unit (a) having a conventional structure as disclosed in Korean Patent No. 10-0815378 is a device structure designed to be used for suturing wound involving narrow tissue injury.

However, in an actual medical procedure, there may be a case where wound involving widespread tissue injury needs to be sutured, and, thus, a clip unit suitable for such a procedure is required.

For example, as shown in FIG. 1a, for the narrow wound of a site "A", a surgical procedure of suturing the wound by picking up (clipping) an edge of the wound with the clip unit a having a conventional structure, but for the relatively wide wound of a site "B", since an arm b of the clip unit a cannot completely cover an edge of the wound, there is a problem that other alternative methods for suture are to be sought.

Meanwhile, in the case of additionally extending the arm b of the clip unit a in order to solve the problem, as shown in FIG. 1b, a turning radius for operating an apparatus (endoscope) c is decreased, and, thus, there is a problem that accuracy in access to a wound site is considerably reduced.

DISCLOSURE

Technical Problem

The present invention is conceived in view of the foregoing problems, and an object of the present invention is to provide a medical clip, a clip unit, and a clip device by which accuracy in access to a site to be treated can be secured and also which can be employed to suture or remove a site involving widespread tissue injury.

Technical Solution

In order to achieve the above-described object, one exemplary embodiment of the present invention provides a medical clip including: a first arm and a second arm between which a target (a site to be treated) is placed and which together squeeze the target; a ring configured to connect one end of the first arm with one end of the second arm; a first ancillary arm articulated with the other end of the first arm; and a second ancillary arm articulated with the other end of the second arm.

According to a preferred example, the medical clip may further include: a first elastic member which is connected between the first arm and the first ancillary arm to provide power for spreading the first arm and the first ancillary arm from each other; and a second elastic member which is connected between the second arm and the second ancillary arm to provide power for spreading the second arm and the second ancillary arm from each other.

According to a preferred example, the first elastic member and the second elastic member may be any one of elastic rubber and a torsion spring.

According to a preferred example, by at least one of a method using an adhesive, a heat-pressing method, a high-frequency attaching method, a photopolymerization method, and a bolt-fixing method, one end of the first elastic member and one end of the second elastic member may be bonded to the first arm and the second arm, respectively, and the other end of the first elastic member and the other end of the second elastic member may be bonded to the first ancillary arm and the second ancillary arm, respectively.

According to a preferred example, in the case where the first ancillary arm and the second ancillary arm are open, the first ancillary arm and the second ancillary arm can be extended in directions dislocated to extension directions of the first arm and the second arm, respectively.

According to a preferred example, each of the first ancillary arm and the second ancillary arm includes multiple joints articulated with each other, and each of the joints can be connected with an elastic member providing power joints for spreading the joints from each other.

According to a preferred example, each of the multiple joints may be rolled and folded into the inner side between the first arm and the second arm.

According to a preferred example, the medical clip may further include: a first fixing lock protruding from any one of the first arm and the first ancillary arm toward the other of them; and a second fixing lock protruding from any one of the second arm and the second ancillary arm toward the other of them.

According to a preferred example, a first inclined surface may be formed at the first arm of the first fixing lock or a surface to be in contact with the first ancillary arm, and a second inclined surface may be formed at the second arm of the second fixing lock or with a surface to be in contact the second ancillary arm.

Also, in order to achieve the above-described object, another exemplary embodiment of the present invention provides a medical clip including: a first arm and a second arm between which a target is placed and which together squeeze the target; a ring configured to connect one end of the first arm with one end of the second arm; a first slot and a second slot formed at the other end of the first arm and the other end of the second arm, respectively; a first ancillary arm of which one end is inserted into the first slot; a first elastic member provided between the first slot and the first ancillary arm and configured to transmit an elastic force; a second ancillary arm of which one end is inserted into the second slot; and a second elastic member provided between the second slot and the second ancillary arm and configured to transmit an elastic force.

According to a preferred example, the first ancillary arm and the second ancillary arm may further include first hooking parts at one ends respectively inserted into the first slot and the second slot, and each of the first slot and the second slot may further include a second hooking part to be combined with the first hooking part.

Moreover, in order to achieve the above-described object, yet another exemplary embodiment of the present invention provides a medical clip unit including: a medical clip that includes a first arm and a second arm between which a target is placed and which together squeeze the target, a ring configured to connect one end of the first arm with one end of the second arm, a first ancillary arm articulated with the other end of the first arm, and a second ancillary arm articulated with the other end of the second arm; a connecting member which is connected to the ring of the medical clip; and a pressing tube which is inserted in a state where the connecting member is connected with the ring.

Also, in order to achieve the above-described object, still another exemplary embodiment of the present invention provides a medical clip device including: the clip unit having the above-mentioned features; a wire which is connected with the connecting member of the medical clip constituting the clip unit, and a tubular body which is inserted into an endoscope and serves as a passage of the clip unit and the connecting member.

Effect of the Invention

According to the present invention, widespread wound can be sutured using a small number of the medical clips, and the widespread wound which cannot be sutured with a conventional clip can be easily sutured. Further, since posture transition of the medical clip according to the present invention is easy in a small space, it can be applied to a surgical procedure of a site to which it is impossible to access or to which a surgical procedure cannot be applied.

DESCRIPTION OF DRAWINGS

FIG. 10c is provided to explain an operation of the clip of FIG. 10a.

DESCRIPTION OF REFERENCE NUMERALS

| | |
|---|---|
| 10: Medical clip | 100: First arm |
| 110: First ancillary arm | 111: Fixing lock |
| 120: Hinge shaft | 130: Elastic member |
| 200: Second arm | 210: Second ancillary arm |
| 220: Hinge shaft | 300: Ring |

BEST MODE

[First Example]

Figure 1A:
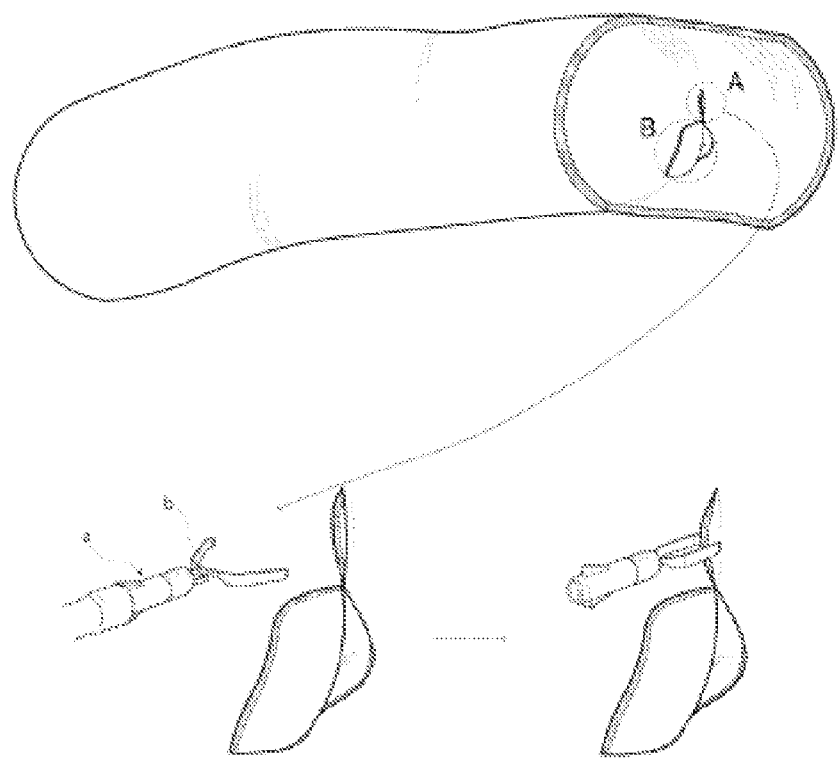
FIGS. 1a and 1b are provided to explain the problem occurring when applying a clip unit having a conventional structure.
Figure 1B:
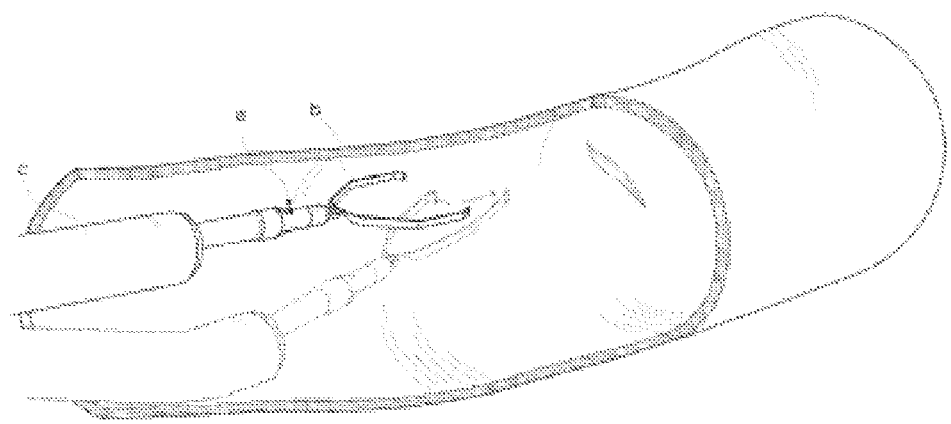
Figure 2:
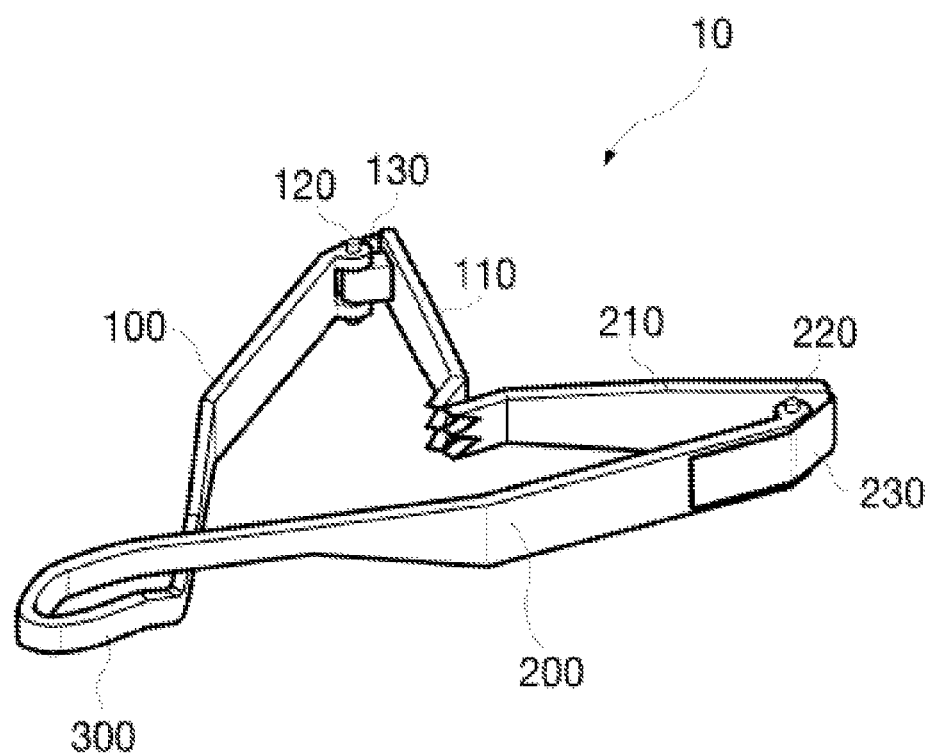
FIG. 2 is a perspective view schematically showing a structure of a medical clip according to a first example of the present invention.
Figure 3A:
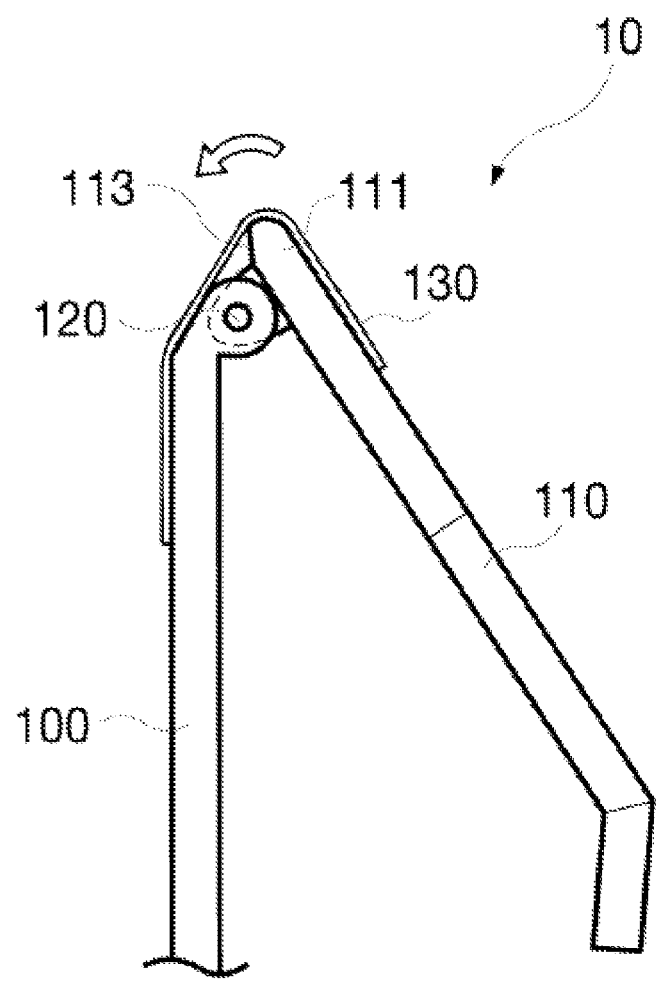
FIGS. 3a and 3b provide a side view and a perspective view, respectively, showing an enlarged joint of the medical clip of FIG. 2.
Figure 3B:
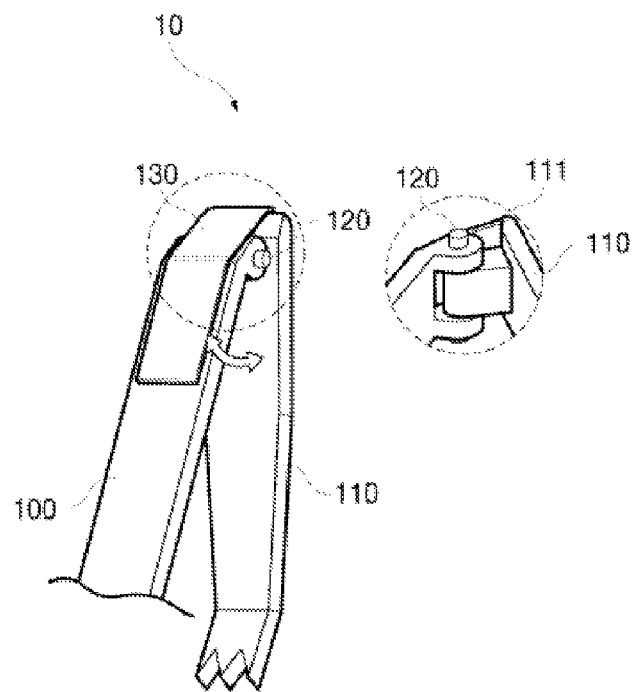

FIG. 2 is a perspective view showing a structure of a medical clip according to a first preferred example of the present invention, and FIGS. 3a and 3b provide a side view and a perspective view, respectively, showing an enlarged joint of the medical clip of FIG. 2.

At first, referring to FIG. 2, a medical clip 10 according to the preferred example of the present invention includes a first arm 100 configured to pick up one edge of a tissue site to be a target (site to be treated) and a second arm 200 configured to pick up the other edge of the site to be treated. At a lower part where the first arm 100 and the second arm 200 are serially connected with each other, the first arm 100 and the second arm 200 are bent and thus form a ring 300. Also, at ends of the first arm 100 and the second arm 200 constituting the medical clip 10, a first ancillary arm 110 and a second ancillary arm 210 foldably connected with each other are provided, respectively. The medical clip 10 may be formed of a metal-made plate such as a plate-spring material, and the like.

The first arm 100 and the second arm 200 have an elastic force in a direction to be spaced apart from each other by the characteristics of the clip structure (e.g., a ring structure and a main body being an elastic material).

Furthermore, the first ancillary arm 110 and the second ancillary arm 210 receive a force that enables the first ancillary arm 110 and the second ancillary arm 210 to be upstanding in an extension direction of the first arm 100 and the second arm 200 by elastic members 130 and 230 (e.g., elastic rubber) as described below, respectively. Herein, the term "force that enables the arms to be upstanding" refers to a force that converts a state of the first ancillary arm 110 and the second arm 210 from a folded state inside the first arm 100 and the second arm 200 to a state parallel or almost parallel to the extension directions of the first arm 100 and the second arm 200.

Meanwhile, the drawing (FIG. 2) shows a state that the first ancillary arm 110 and the second ancillary arm 210 are in contact with each other, and, thus, their upstanding postures are suppressed.

That is, the medical clip 10 according to the preferred example of the present invention is upstanding while the respective ancillary arms 110 and 210 are rotated around the hinge shafts 120 and 220 according to elastic forces of the elastic members 130 and 230 at the time when an abutting state between the first ancillary arm 110 and the second ancillary arm 210 is released as a distance between the first arm 100 and the second arm 200 increases.

On the other hand, in the drawings related to the examples of FIGS. 2 to 9 attached to the present specification, although the first arms 100 and 100″ and the first ancillary arms 110, 110′, and 110‴, and second arms 200 and 200″, and second ancillary arms 210, 210′, and 210‴ are illustrated as being rotated around the hinge shafts 120 and 220, the medical clips 10, 10′, 10″, and 10″″ of the present invention are not necessarily limited to this structure. That is, the medical clips 10, 10′, 10″, and 10″″ of the present invention may include all forms of articulation structure between the first arms 100 and 100″ and the first ancillary arms 110, 110′, and 110‴, and between the second arms 200 and 200″ and the second ancillary arms 210, 210′, and 210‴. However, in the following description, for convenience, it will be described that the medical clips 10, 10′, 10″, and 10″″ have a structure being articulated by the hinge shafts 120 and 220 as an example.

Hereinafter, with reference to FIGS. 3a and 3b, a joint structure of the medical clip 10 according to the first example of the present invention will be explained. The first ancillary arm 110 is hinge-linked to the first arm 100 by the hinge shaft 120, and the elastic member 130 configured to provide a force that rotates the first ancillary arm 110 is provided between the first arm 100 and the first ancillary arm 110.

According to the preferred example, the elastic member 130 may be belt-like elastic rubber having an elastic recovering force.

According to the preferred example, one end of the elastic member 130 may be bonded to the first arm 100 and the other end thereof may be bonded to the first ancillary arm 110 by at least one of a method using an adhesive, a heat-pressing method, a high-frequency attaching method, a photopolymerization method, and a bolt-fixing method. For example, one end of the elastic member 130 is bond and fixed to a hinge of the first arm 100 by the heat-pressing method, and likewise, the other end of the elastic member 130 is bond and fixed to a hinge of the first ancillary arm 110 by the heat-pressing method, thereby providing the elastic member 130 between the first arm 100 and the first ancillary arm 110. Also, as another example, one end and the other end of the elastic member 130 may be assembled and fixed to hinges of the first arm 100 and the first ancillary arm 110, respectively, by the bolt-fixing method.

On the hinge side end of the first ancillary arm 110, a fixing lock 111 extending to a length beyond the hinge shaft 120 is formed.

The fixing lock 111 functions as a hinge stopper controlling a rotation of the first ancillary arm 110 within a certain angle range. A lower end surface of the fixing lock 111 in a hinge side direction is brought into contact with one side surface of the first arm 100 when the first ancillary arm 110 is fully upstanding, and, thus, any further rotation can be suppressed.

According to the preferred example, at the lower end surface of the fixing lock 111 in the hinge side direction, there is formed an inclined surface 113 that enables the first ancillary arm 110 to be upstanding at a desired angel with respect to the first arm when the first ancillary arm 110 is fully upstanding. Therefore, an upstanding angle of the first ancillary arm 110 can be controlled. For example, in order to increase a width between the first arm 100 and the first ancillary arm 110, the inclined surface 113 is formed so as to have a smooth angle, whereas in order to decrease the width between the first arm 100 and the first ancillary arm 110, the inclined surface 113 is formed so as to have a sharp angle.

On the other hand, in the drawings related to the examples of the FIGS. -3 to 9 attached to the present specification, although the fixing lock 111 and 111′ are illustrated as being formed on the first ancillary arms 110, 110′, and 110‴, the medical clips 10, 10′, 10″, and 10″″ of the present invention are not necessarily limited to this structure. That is, the medical clips 10, 10′, 10″, and 10″″ of the present invention include the first arms 100 and 100″ in which a fixing lock controlling a rotation of the first ancillary arms 110, 110′, and 110‴ is formed. However, in the following description, for convenience, it will be described that the fixing lock 111 and 111′ are formed at the first ancillary arms 110, 110′, and 110‴ as an example.

The joint structure between the second arm 200 and the second ancillary arm 210 is the same as the above-described joint structure between the first arm 100 and the first ancillary arm 110, and therefore, the detailed structure of the above-described hinge shaft 120, elastic rubber (belt-like elastic rubber) 130, and fixing lock 111 can also be applied to the second arm 200 and the second ancillary arm 210.

Figure 4:
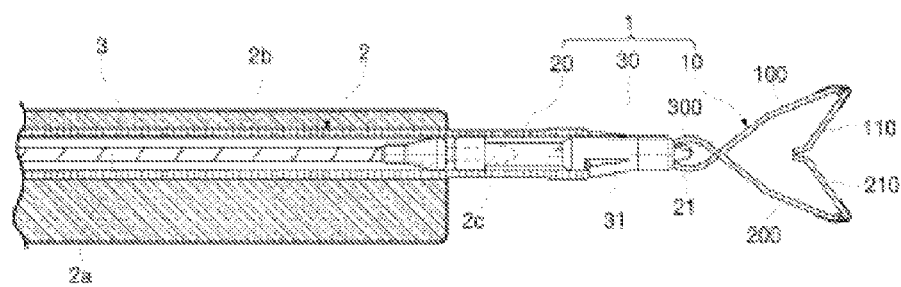
FIG. 4 is provided to schematically illustrate a structure of a clip unit to which the medical clip according to the first example of the present invention is applied.

FIG. 4 is provided to explain a clip unit and a clip device to which the medical clip according to the preferred example of the present invention is applied.

The clip unit 1 according to the preferred example of the present invention is configured to ultimately control the clip 10 to make a motion of grabbing (i.e. a motion of picking up) an edge of "the site to be treated" by controlling motions of the first arm 100 (including the first ancillary arm 110) and the second arm 200 (including the second ancillary arm 210) constituting the clip 10.

Further, the clip device 1 and 2 according to the preferred examples of the present invention is a combination of the clip unit 1 and the clip unit-controlling device 2 that controls the clip unit 1. Herein, the clip unit-controlling device 2 directly controls a motion of the clip unit 1 while being inserted into a treatment instrument insertion channel of an endoscope 3 in a state being connected with the clip unit 1.

In addition, the term "the site to be treated" herein includes tissue that needs to be sutured due to wound, etc., and tissue that needs to be removed due to cancer cells. Hereinafter, although there will be explained the clip unit 1 in an example case where a suture procedure is to be made due to occurrence of wound on the organ, etc. for convenience, the clip unit 1 being the present invention can also be applied to a tissue removal procedure as well as a tissue suturing procedure.

The clip unit 1 includes the medical clip 10, a connecting member 20 the ring 300 of the medical clip 10, and a pressing tube 30 into which the connecting member 20 is inserted while the ring 300 of the medical clip 10.

The connecting member 20 is a member which enters into and withdraws from the cylindrical pressing tube 30. A hook structure 21 capable of the ring 300 of the clip 10 is formed at a front end of the connecting member 20. The drawing (FIG. 4) shows a state where the hook structure 21 the ring 300 is deeply inserted into the interior of the pressing tube 30 to a predetermined depth. Further, at a base end of the connecting member 20, a connecting structure (not shown) connected with a connecting mechanism 2c of the clip unit-controlling device 2 is formed. The drawing (FIG. 4) shows a state where the conical connecting structure 2c formed at a front end of a wire 2a of the clip unit-controlling device 2 is connected with the connecting structure (not shown) of the connecting member 20.

The pressing tube 30 is formed into a generally cylindrical shape, and a hooking structure 31 being able to be protruded or recessed is formed on the outer peripheral surface of the body. The hooking structure 31 controls penetration of the pressing tube 30 through a tubular body 2b of the clip unit-controlling device 2 and insertion of the pressing tube 30 into the tubular body 2b.

FIGS. 5a to 5e are provided to explain a picking-up (clipping) mechanism of the clip unit 1 to which the medical clip 10 according to the preferred example of the present invention is applied.

Figure 5A:
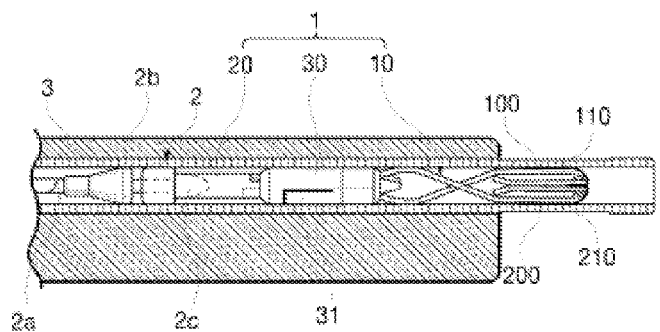
FIGS. 5a to 5e are provided to explain a picking-up (clipping) mechanism of the clip unit to which the medical clip according to the first example of the present invention is applied.

As shown in FIG. 5a, by manipulation of a user, the clip unit 1 is inserted into the tubular body 2b while being connected to the connecting mechanism 2c formed at the front end of the wire 2a constituting the clip unit-controlling device 2 and penetrates into the organ of a patient. At this time, the first arm 100 and the second arm 200 of the medical clip 10 are substantially parallel to each other, and each of the first ancillary arm 110 and the second ancillary arm 210 is in a state of being folded into the inner side of the first arm 100 and the second arm 200. On the other hand, FIG. 5a shows a state where the hooking structure 31 formed on the outer peripheral surface of the pressing tube 30 of the clip unit 1 is compressed and recessed by the tubular body 2b.

Figure 5B:
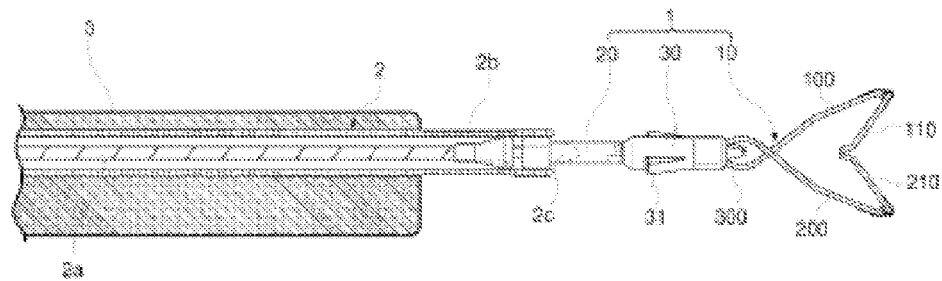

Then, as shown in FIG. 5b, in the case where the wire 2a of the clip unit-controlling device 2 is pushed into the front end side of the tubular body 2b by manipulation of the user, the clip unit 1 passes through the front end of the tubular body 2b and withdrawn to the outside of the tubular body 2b. At this time, as the medical clip 10 is completely released from the tubular body 2b, the first arm 100 and the second arm 200 are spread to the extent of an elastic force of the materials constituting the clip 10. However, since the first ancillary arm 110 and the second ancillary arm 210 abut on each other, their upstanding postures are suppressed (i.e. they are still folded). On the other hand, FIG. 5b shows a state where the hooking structure 31 formed on the outer peripheral surface of the pressing tube 30 of the clip unit 1 is outwardly protruded as it is withdrawn to the outside of the tubular body 2b.

Figure 5C:
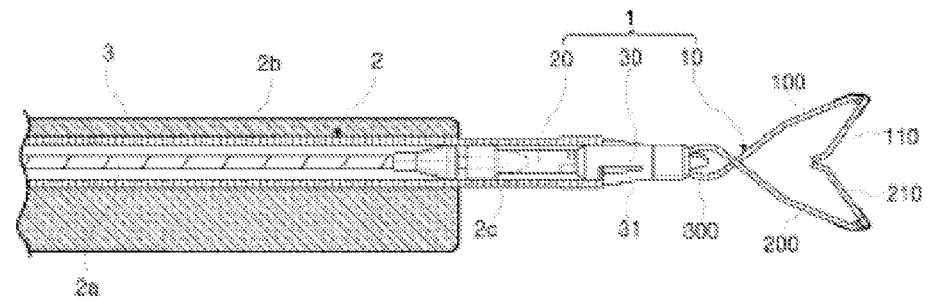

Then, as shown in FIG. 5c, in the case where the wire 2a of the clip unit-controlling device 2 is pulled toward the user by manipulation of the user, the clip unit 1 connected to the wire 2a is also pulled toward the user while the hooking structure 31 protruded from the outer peripheral surface of the pressing tube 30 is hooked at the front end of the tubular body 2b of the clip unit-controlling device 2, and therefore, the further insertion of the pressing tube 30 of the clip unit 1 into the tubular body 2b is suppressed. The medical clip 10 in FIG. 5c is the same as shown in FIG. 5b.

Figure 5D:
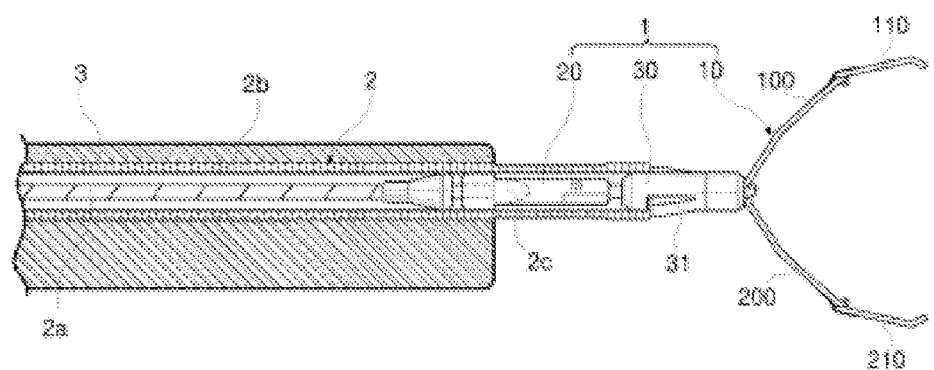

Then, as shown in FIG. 5d, while the insertion of the pressing tube 30 of the clip unit 1 into the tubular body 2b by the protruded hooking structure 31 is suppressed, in the case where the wire 2a of the clip unit-controlling device 2 is more pulled toward the user by manipulation of the user, the connecting member 20 of the clip unit 1 connected to the wire 2a is further pulled toward the user (at this time, insertion of the pressing tube 30 into the tubular body 2b is still suppressed) and the ring 300 of the medical clip 10 is forced to be inserted into the pressing tube 30. Thus, the first arm 100 and the second arm 200 of the clip 10 are further spread than the state of FIG. 5c, and as an abutting state of the first ancillary arm 110 and the second ancillary arm 210 folded inside the first arm 100 and the second arm 200 is released, the first ancillary arm 110 and the second ancillary arm 210 are instantaneously in an upstanding state by an elastic force of the elastic member 130.

Figure 5E:
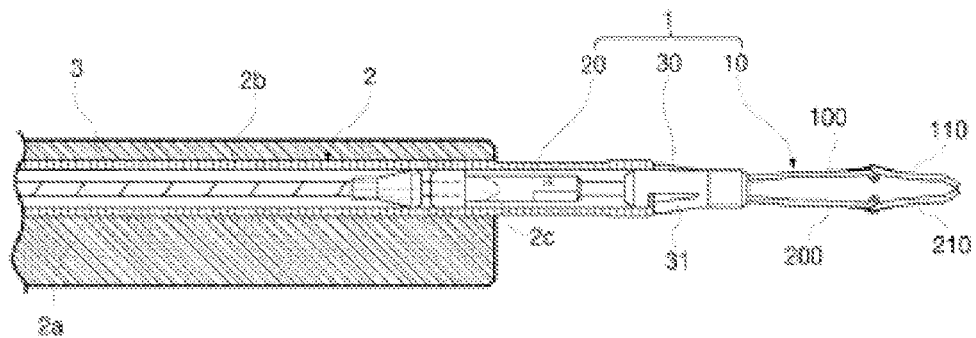

Then, as shown in FIG. 5e, in the case that the wire 2a of the clip unit-controlling device 2 is pulled toward the user by manipulation of the user, as the connecting member 20 of the clip unit 1 connected to the wire 2a is further pulled toward the user (insertion of the pressing tube 30 into the tubular body 2b is still suppressed), a lower side part of the first arm 100 and a lower side part of the second arm 200 are forced to be inserted into the pressing tube 30. As the lower side part of the first arm 100 and the lower side part of the second arm 200 are forced to be inserted into the pressing tube 30, the first arm 100 and the second arm 200 are close to each other (i.e. make a picking-up motion). If the first arm 100 and the second arm 200 are in a fully parallel state as the lower side part of the first arm 100 and the lower side part of the second arm 200 are forced to be further inserted into the pressing tube 30, a grabbing force (i.e., picking-up force) between the first ancillary arm 110 and the second ancillary arm 210 is maximized.

The clip unit 1 to which the medical clip 10 according to the preferred example of the invention is applied can make a motion of grabbing (i.e. picking up) the edge of the site to be treated according to the motions of the FIGS. 5a to 5e as described above. In particular, since the medical clip 10 according to the preferred example of the present invention adopts the first ancillary arm 110 and the second ancillary arm 210 which are folded when approaching the site to be treated and open just before picking up the edge of the site to be treated, it is very useful for suturing or removing a site involving widespread tissue injury.

[Second Example]

Figure 6A:
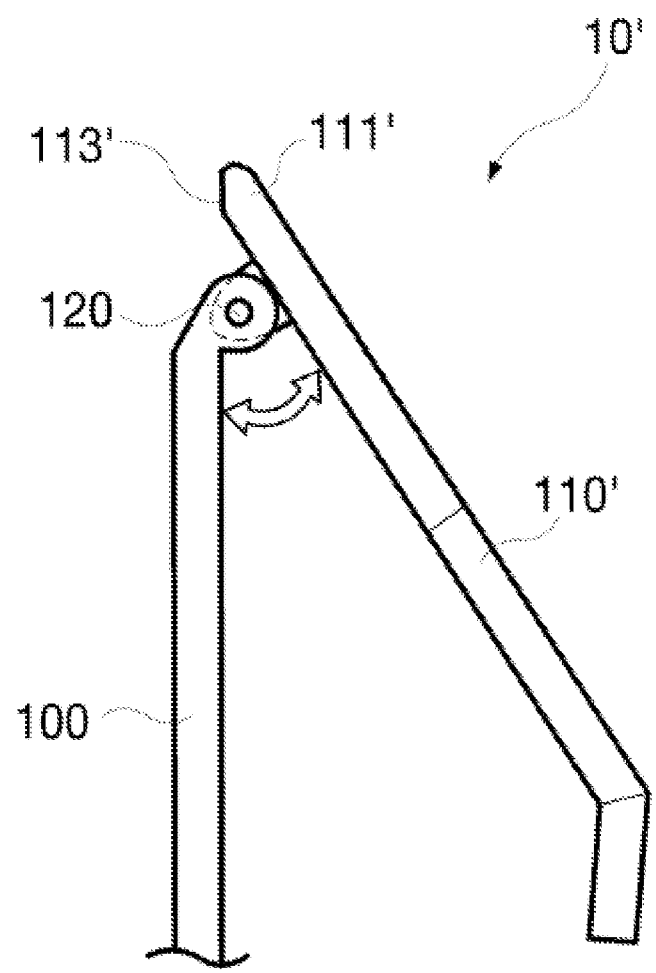
FIGS. 6a and 6b provide a side view and a perspective view, respectively, showing an enlarged joint of a medical clip according to a second example of the present invention.
Figure 6B:
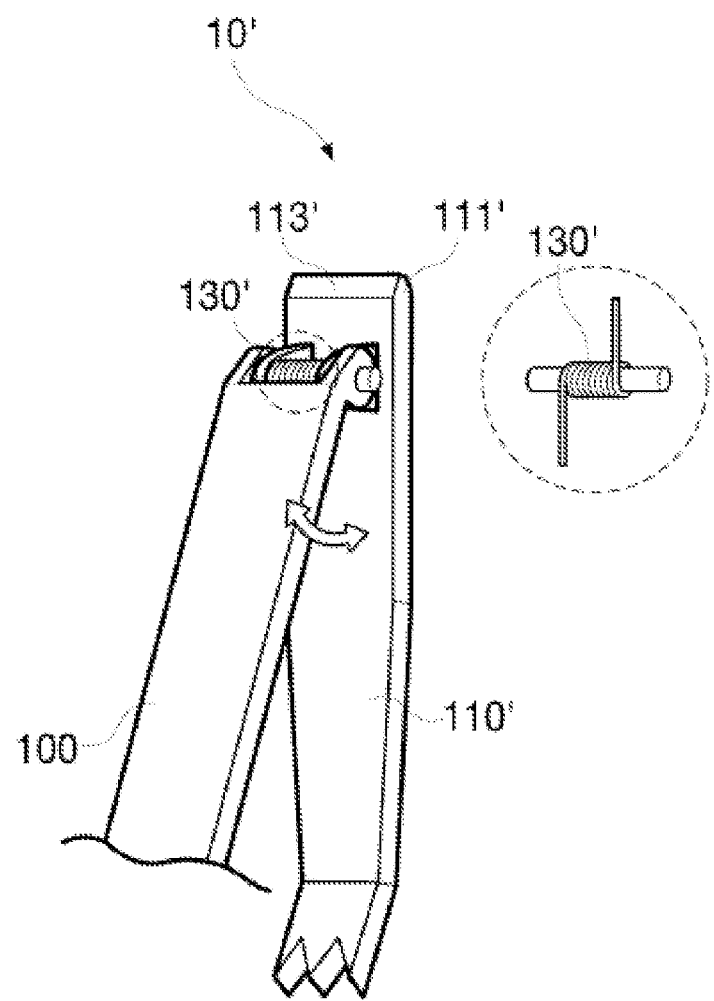

FIGS. 6a and 6b provide a side view and a perspective view, respectively, showing an enlarged joint of a medical clip according to a second example of the present invention.

A medical clip 10' according to the second preferred example of the present invention has the same structure as that of the first example except that only the joint structure of the clip 10' is different from that of the first example described above.

Hereinafter, although the medical clip 10' according to the second preferred example of the present invention will be explained with reference to FIGS. 6a and 6b, the explanation herein is made based on the differences from the first example described above (i.e. the joint structure of the clip 10'), and explanation of the other parts identical with those of the first example will be omitted.

As shown in FIGS. 6a and 6b, in the joint structure of the medical clip 10' according to the second preferred example of the present invention, a first ancillary arm 110' is hinge-linked to the first arm 100 by the hinge shaft 120, and an elastic member 130' configured to provide a force that rotates the first ancillary arm 110' in a direction in which the first arm 100 and the first ancillary arm 110' are separated from each other is installed on the outer peripheral surface of the hinge shaft 120. According to the preferred example, the elastic member 130' may be a torsion spring.

On the hinge side end of the first ancillary arm 110', a fixing lock 111' extending to a length beyond the hinge shaft 120 is formed.

The fixing lock 111' functions as a hinge stopper controlling a rotation of the first ancillary arm 110' within a certain angle range. A lower end surface of the fixing lock 111' in a hinge side direction is brought into contact with one side surface of the first arm 100 when the first ancillary arm 110' is fully upstanding, and, thus, any further rotation is inhibited.

According to the preferred example, at the lower end surface of the fixing lock 111' in the hinge side direction, there is formed an inclined surface 113' that is cut so as to enable the first ancillary arm 110' to be upstanding at a desired angel with respect to the first arm when the first ancillary arm 110' is fully upstanding. Therefore, an upstanding angle of the first ancillary arm 110' can be controlled.

The joint structure between the second arm 200 and the second ancillary arm (not shown) may be the same as the above-described joint structure between the first arm 100 and the first ancillary arm 110'. That is, the detailed structure of the above-described hinge shaft 120, elastic member 130' and fixing lock 111' can be equally applied to the joint structure between the second arm 200 and the second ancillary arm (not shown).

[Third Example]

Figure 7A:
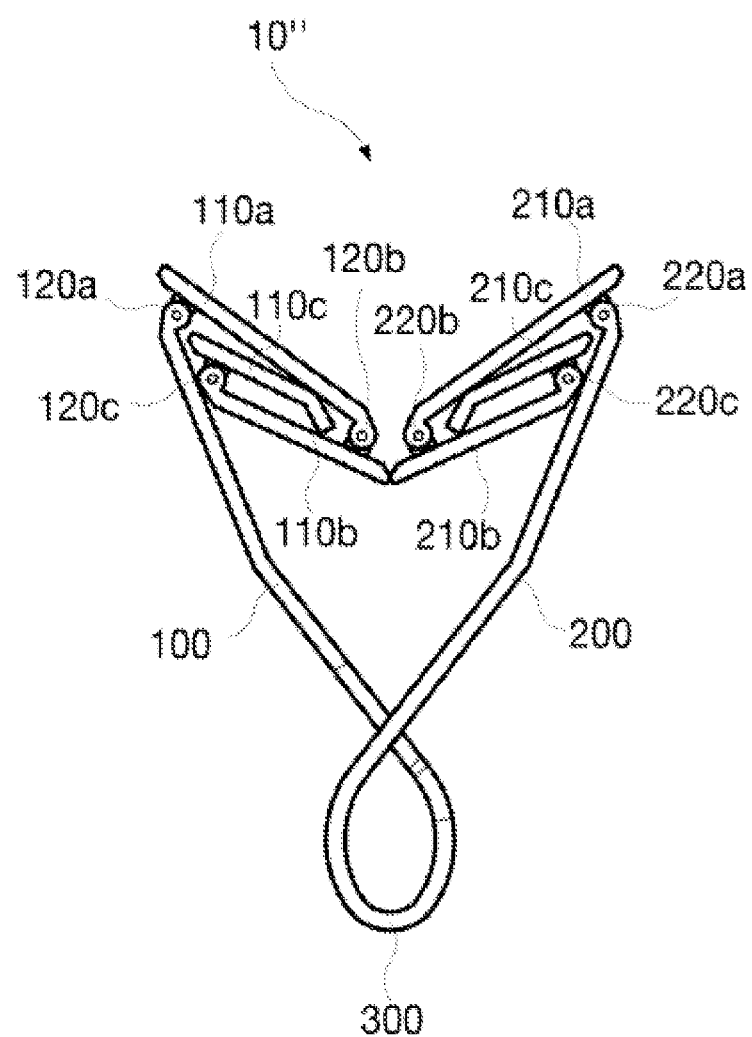
FIG. 7a is a perspective view schematically showing a structure of a medical clip according to a third example of the present invention.
Figure 7B:
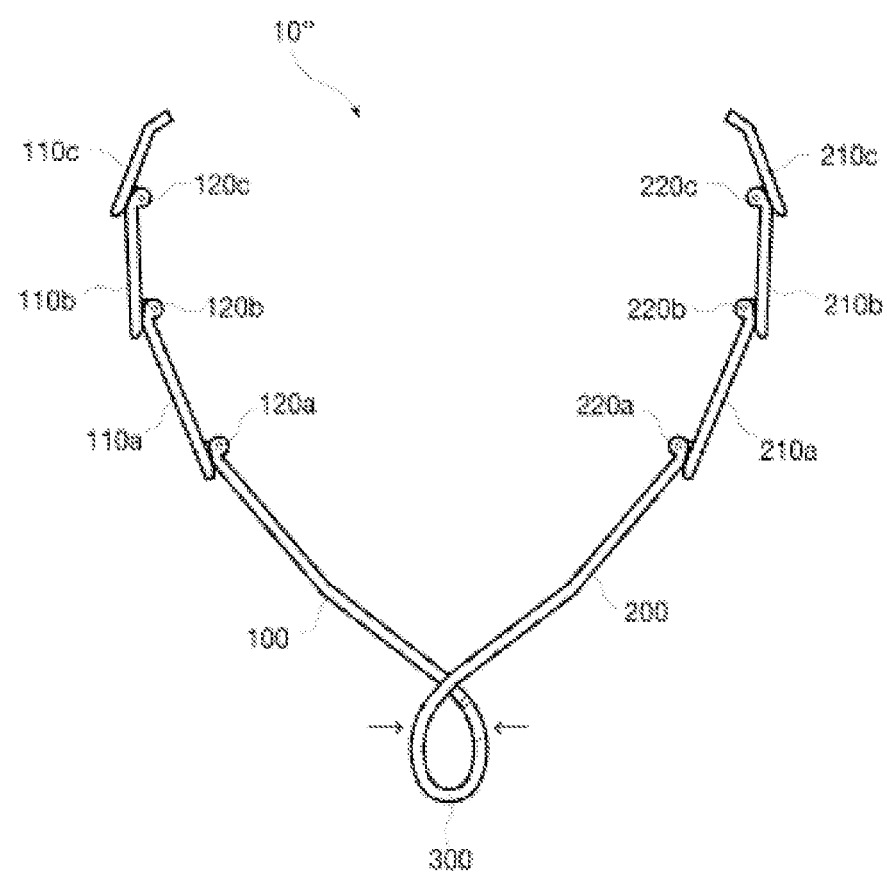
FIG. 7b is provided to show that all of multi-stage ancillary joints constituting the clip of FIG. 7a are in an upstanding state.

FIG. 7a is a perspective view schematically showing a structure of a medical clip according to a third preferred example of the present invention, and FIG. 7b is provided to show that all of multi-stage ancillary joints constituting the clip of FIG. 7a are in an upstanding state.

The medical clip 10" according to the third preferred example of the present invention is the same as that of the above-described first example in all of the structure except that the first ancillary arm 110 and the second ancillary arm 210 in the first example are formed of the multi-stage joints.

Hereinafter, although the medical clip 10" according to the third preferred example of the present invention will be explained with reference to FIGS. 7a and 7b, the explanation herein is made based on the differences from the first example described above (i.e. the first ancillary arm 110 and the second ancillary arm 210 formed of the multi-stage joints), and explanation of the other parts identical with those of the first example will be omitted.

Figure 8A:
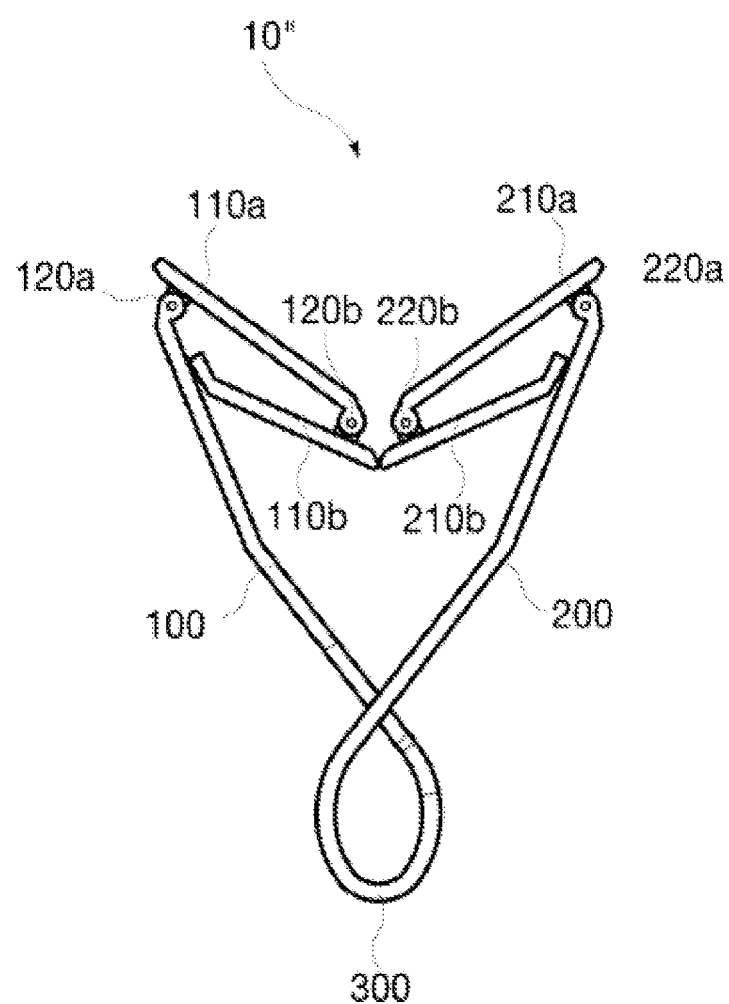
FIG. 8a is a perspective view schematically illustrating another structure of the medical clip according to the third example of the present invention, and FIG. 8b provided to show that all of multi-stage ancillary joints constituting the clip of FIG. 8a are in an upstanding state.
Figure 8B:
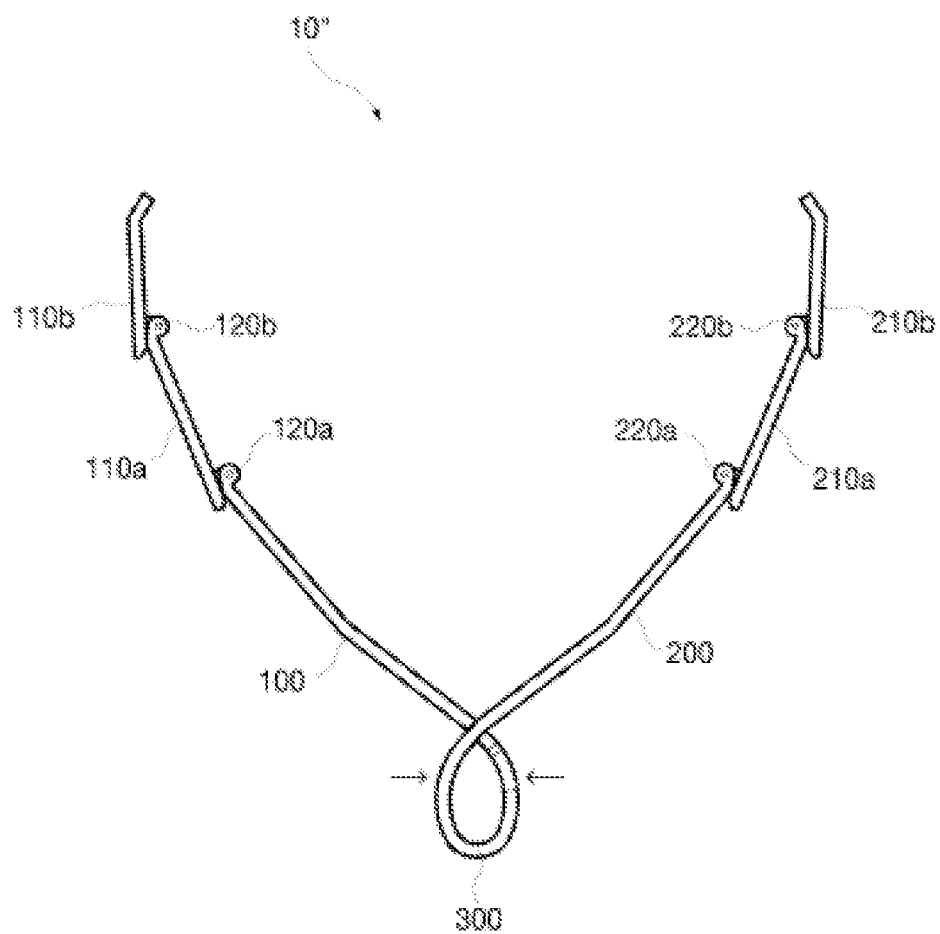

In addition, since the medical clip 10" according to the third preferred example of the present invention has a feature in that the first and second ancillary arms are formed of the multi-stage joints, one skilled in the art could understand that the first and second ancillary arms can be formed of at least three or more stages. That is, although FIGS. 7a and 7b illustrate an example where each of the first ancillary arm and the second ancillary arm is formed of joints of four stages, the medical clip 100" according to the third preferred example of the present invention may also include the first ancillary arm and the second ancillary arm each formed of joints of three stages, as shown in FIGS. 8a and 8b.

As shown in FIG. 7a, in the first arm 100's side of the medical clip 10" according to the third preferred example of the present invention, a first ancillary joint 110a is hinge-linked with the first arm 100 by a hinge shaft 120a, a second ancillary joint 110b is hinge-linked to the first ancillary joint 110a by a hinge shaft 120b, and a third ancillary joint 110c configured to make a motion of directly picking up the site to be treated is hinge-linked to the second ancillary arm 110b by a hinge shaft 120c.

According to the preferred example, the elastic member (not shown) configured to transmit a rotation force between two hinge-linked joints 110 to 110a, 110a to 110b, and 110b to 110c may be provided around each of the hinge shafts 120a to 120c.

Further, according to the preferred example, at a hinge side end of each of the first to third ancillary joints 110a to 110c, a hooking part (not shown) extending to a length beyond each of the hinge shafts 120a to 120c may be formed. Each of the hooking part (not shown) herein functions as a hinge stopper controlling rotations of the first to third ancillary arms 110a to 110c within a certain angle range.

In addition, the multi-stage ancillary joints 210a to 210c of the second arm 200 may be constructed in the same manner as the above-described multi-stage ancillary joints 110a to 110c of the first arm 100.

Since the medical clip 10" according to the third preferred example of the present invention adopts the multi-stage ancillary joints 110a to 110c and 210a to 210c which are folded inside the first arm 100 and the second arm 200 (i.e. the multi-stage ancillary joints 110a to 110c and 210a to 210c are rolled and folded into the inner side of the first arm 100 and the second arm 200) when approaching the site to be treated and are upstanding in multiple stages just before picking up the edge of the site to be treated, it is very useful for suturing or removing a site involving relatively widespread tissue injury FIG. 7b shows a state where that all of the multi-stage ancillary joints 110a to 110c and 210a to 210c of the first arm 100 and the second arm 200 of the medical clip 10" according to the third preferred example of the present invention are upstanding.

[Fourth Example]

Figure 9A:
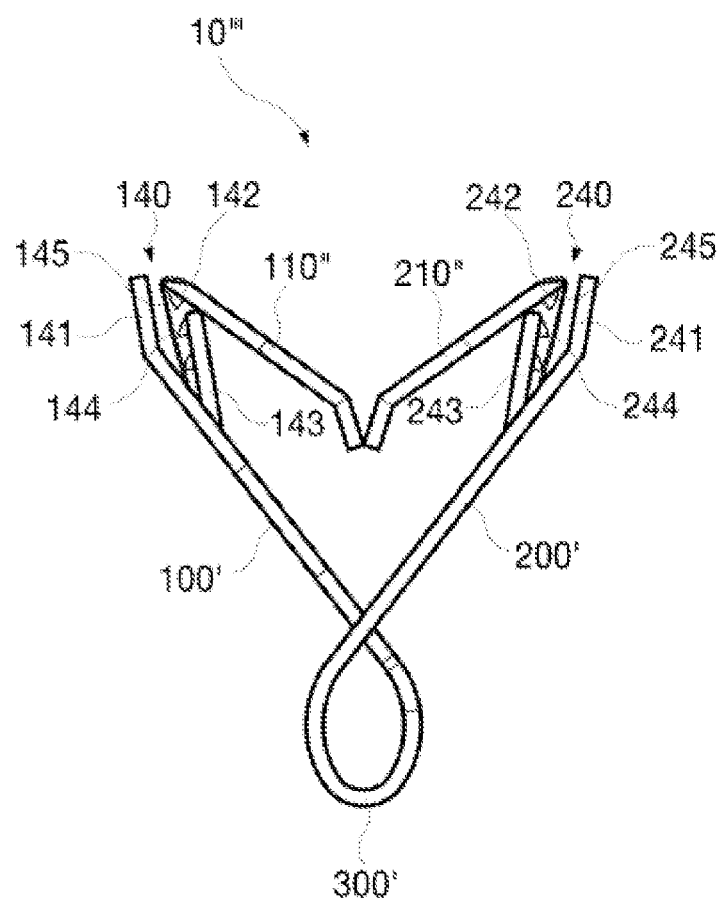
FIG. 9a is a perspective view schematically illustrating a structure of a medical clip according to a fourth example of the present invention.
Figure 9B:
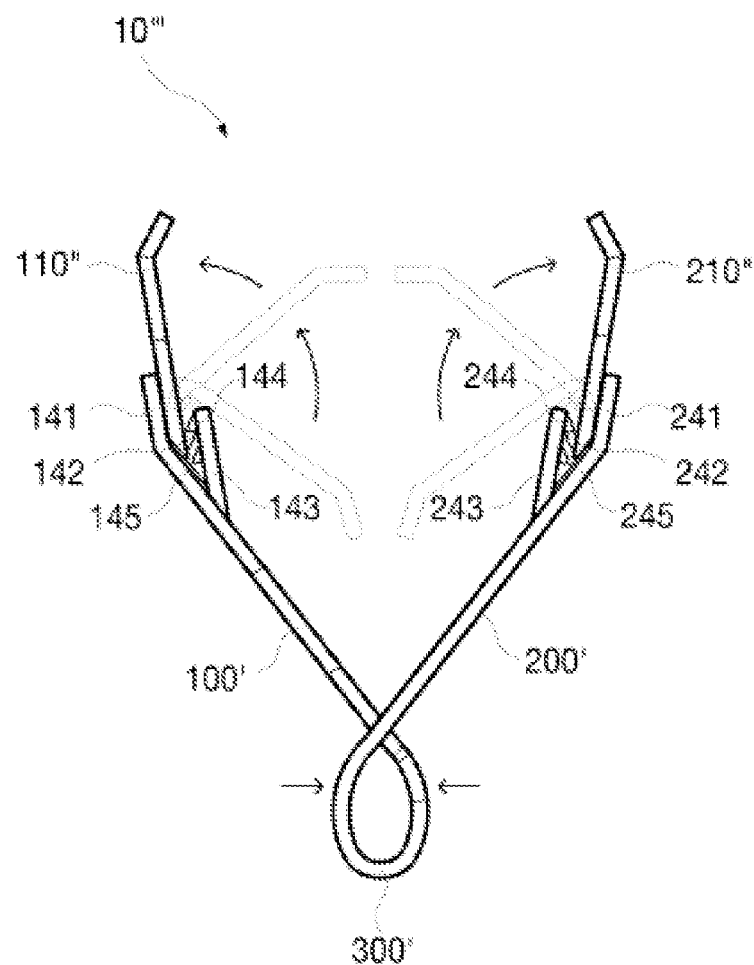
FIG. 9b is provided to show that the first ancillary arm and the second ancillary arm constituting the clip of FIG. 9a are in an upstanding state.

FIG. 9a is a perspective view schematically illustrating a structure of a medical clip 10''' according to a fourth example of the present invention, and FIG. 9b is provided to explain that the first ancillary arm 110" and the second ancillary arm 210" constituting the clip of FIG. 9a make upstanding postures.

At first, referring to FIG. 9a, the medical clip 10''' according to the fourth preferred example of the present invention includes a first arm 100' configured to pick up one edge of a site to be treated (hereinafter, referred to as "target") and a second arm 200' configured to pick up the other edge of the target. The first arm 100' and the second arm 200' are bent and form a ring 300' at a lower part where the first arm 100' and the second arm 200' are serially connected to each other. Also, at ends of the first arm 100' and the second arm 200' constituting the medical clip 10', slot portions 140 and 240 for inserting ancillary arms are formed, respectively, and the slot portion 140 of the first arm 100' and the slot portion 240 of the second arm 200' are connected to a first ancillary arm 110" and a second ancillary arm 210" via elastic members 145 and 245, respectively.

Such the medical clip 10''' is formed of, for example, a metal-made plate such as a plate-spring material, and the like.

The first arm 100' and the second arm 200' have an elastic force in a direction to be spaced apart from each other by the characteristics of the clip structure (e.g., a ring structure and a main body being an elastic material).

Furthermore, the first ancillary arm 110" and the second ancillary arm 210" receive a force in a direction to be inserted into slots 140 and 240 for inserting ancillary arms by the elastic member 145 and 245 (e.g., elastic rubber) extended from and connected to the slot 140 and 240.

On the other hand, the drawing (FIG. 9a) shows a state where the first ancillary arm 110" and second ancillary arm 210" are in contact with each other, and, thus, insertions of the ancillary arms 110" and 210" into the into the slots 140 and 240 are suppressed.

That is, each of the ancillary arms 110" and 210" is upstanding while the respective ancillary arms 110" and 210" are inserted into the slots 140 and 240, respectively, according to elastic forces of the elastic members 145 and 245 at the time when an abutting state between the first ancillary arm 110" and the second ancillary arm 210" is released as a distance between the first arm 100' and the second arm 200' increases by manipulating the clip unit-controlling device 2.

According to the preferred example, a slot 140 for inserting an ancillary arm may be constructed in the form forming an inner space (slot) by a first bent part 141 being the outermost bent part at an end of the plate-spring material forming the first arm 100' and a second bent part 143 formed by being spaced apart with a certain distance from the first bent part 141. Likewise, a slot 240 for inserting an ancillary arm may be constructed in the form forming an inner space (slot) by a first bent part 241 being the outermost bent part at an end of the plate-spring material forming the first arm 200' and a second bent part 243 formed by being spaced apart with a certain distance from the first bent part 241.

Further, according to the preferred example, one or more hooking parts 144 and 244 suppressing deviation of the first ancillary arm 110" and the second ancillary arm 210" after being inserted into the slots 140 and 240 may be formed in slots of the slots 140 and 240 for inserting ancillary arms, respectively. For example, each of the hooking parts 144 and 244 may be formed to have a structure of which a width gradually increases toward a bottom surface of the slot.

Also, according to the preferred example, other hooking parts 142 and 242 to be hooked by the hooking parts 144 and 244 may be formed on each of the first ancillary arm 110" and the second ancillary arm 210", respectively.

Further, according to the preferred example, the elastic members 145 and 245 may be bonded and fixed on the bottom surfaces of the slots formed on the slots 140 and 240, or may be bonded and fixed on inner walls surfaces of the slots.

Then, upstanding motions of the first ancillary arm 110" and the second ancillary arm 210" of the medical clip 10''' according to the fourth preferred example of the present invention will be explained with reference to FIG. 9b. The first ancillary arm 110" and the second ancillary arm 210" receive a force that enables the first ancillary arm 110" and the second ancillary arm 210" to be inserted into the slots 140 and 240 for inserting ancillary arms by the elastic members 145 and 245 extended from and connected to the slots 140 and 240, respectively.

However, if a spreading angle between the first arm 100' and the second arm 200' is small, since the first ancillary arm 110" and the second ancillary arm 220" can be brought into contact with each other, their upstanding motions (insertions into the slots 140 and 240) are suppressed.

Meanwhile, the first ancillary arm 110" and the second ancillary arm 210" are inserted into the slots 140 and 240 by being guided by the elastic member 145 and 245 at the time when an abutting state between the first ancillary arm 110" and the second ancillary arm 210" is released as a distance between the first arm 100' and the second arm 200' increases by manipulating the clip unit-controlling device 2. This state is shown in FIG. 9b.

Since the medical clip 10''' according to the fourth preferred example of the present invention adopts a structure of the first ancillary arm 110" and the second ancillary arm 210" which are folded when approaching the site to be treated and are inserted (upstanding) into the slots 140 and 240 just before picking up the edge of the site to be treated, it is very useful for suturing or removing a site involving widespread tissue injury.

[Fifth Example]

Figure 10A:
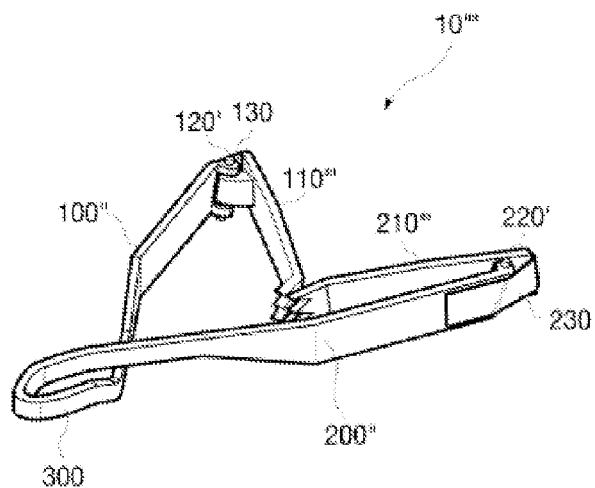
FIG. 10a is a perspective view schematically illustrating a structure of a medical clip according to a fifth example of the present invention.
Figure 10B:
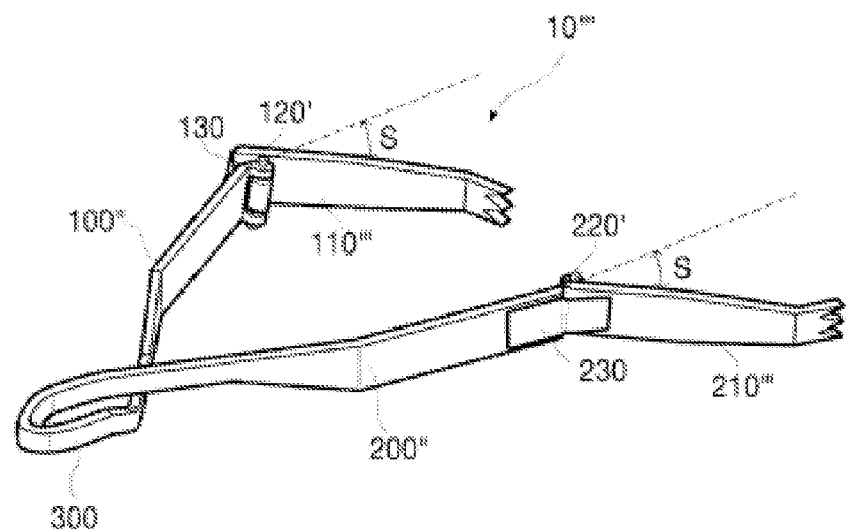
FIG. 10b is provided to show a state where the first ancillary arm and the second ancillary arm are open.
Figure 10C:
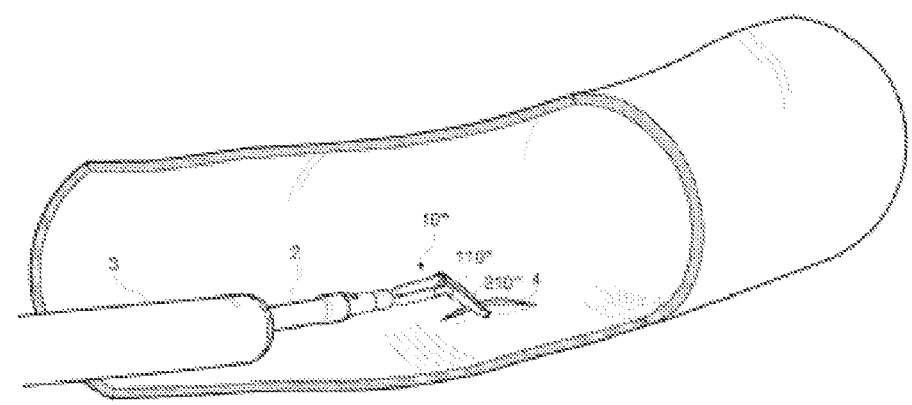

FIG. 10a is a perspective view schematically illustrating a structure of a medical clip according to a fifth preferred example of the present invention, and FIG. 10b is provided to show a state where the first and second ancillary arms 110''' and 210''' are fully open, and FIG. 10c is provided to explain an operation of the clip of FIG. 10a.

As shown in FIG. 10a, at each end of the first arm 100" and the second arm 200" constituting the medical clip 10'''' according to the fifth preferred example of the present invention, there are provided the first ancillary arm 110''' and the second ancillary arm 210''' being connected in a structure where the first ancillary arm 110''' and the second ancillary arm 210''' can be open in an inclined direction in a side view. The other parts are the same as those of the medical clip 10 of the first example.

Herein, the term "structure where the ancillary arms can be open in an inclined direction in a side view" refers to a structure where extension directions of the first ancillary arm 110''' and the second ancillary arm 210''' are dislocated by a predetermined angle from the extension directions of the first arm 100" and the second arm 200" in a side view when the first ancillary arm 110''' and the second ancillary arm 210''' are fully open according to the respective hinge shafts 120' and 220', and the extension directions of the first ancillary arm 110''' and the second ancillary arm 210''' are folded with those of the first arm 100" and the second arm 200" in a side view when the first ancillary arm 110''' and the second ancillary arm 210''' are folded according to the respective hinge shafts 120' and 220'.

Also herein, the state where the extension directions of the first ancillary arm 110''' and the second ancillary arm 210''' are dislocated by a predetermined angle from the extension directions of the first arm 100" and the second arm 200" means that first ancillary arm 110''' and the second ancillary arm 210''' are bent from the first arm 100" and the second arm 200" by any one angle of 0° to 180° in a side view. On the other hand, a bent angle of the first ancillary arm 110''' and the second ancillary arm 210''' can be achieved by modifying the structures of the hinge shafts 120' and 220' as described above. For example, in the case where the hinge shafts 120' and 220' are to be inclined by 45°, the bent angle of the first ancillary arm 110''' and the second ancillary arm 210''' is also 45°. Similarly, by modifying the structures of the hinge shafts 120' and 220', the first ancillary arm 110''' and the second ancillary arm 210''' can be formed to have a bent angle of 60°, 90°, and 120°.

Meanwhile, FIG. 10a shows that each of the joints of the first arm 100" and the second arm 200" constituting the medical clip 10'''' is formed by the hinge shaft 120' inclined by about 45°.

FIG. 10b shows a state where the first ancillary arm 110''' and the second ancillary arm 210''' of the medical clip 10'''' according to the fifth example of the present invention are open from the first arm 100" and the second arm 200", respectively.

That is, the medical clip 10'''' according to the fifth example of the present invention is open while the respective ancillary arms 110''' and 210''' are rotated around the hinge shaft 120' and 220', respectively, according to elastic forces of the elastic members 130 and 230 at the time when an abutting state between the first ancillary arm 10''' and the second ancillary arm 210''' is released as a distance between the first arm 100" and the second arm 200' increases. Also, when the respective ancillary arm 110" and 210''' are fully open from the first arm 100''' and the second arm 200''', the extension directions of the first ancillary arm 110''' and the second ancillary arm 210''' are dislocated by a predetermined angle (S) from those of the first arm 100" and the second arm 200" in a side view.

Since the medical clip 10'''' according to the fifth preferred example of the invention adopts a structure being folded when approaching the site to be treated and open just before picking up the edge of the site to be treated, it is very useful for suturing or removing a site involving widespread tissue injury.

In particular, the medical clip 10'''' according to the fifth preferred example of the present invention is suitable for treatment of wound which is formed at a site which is difficult to access with a conventional medical clip because the first ancillary arm 110''' and the second ancillary arm 210''' in an open state are bent by the predetermined angle (S) from the first arm 100'' and the second arm 200''. For example, as shown in FIG. 10c, even if a wound site 4 is placed vertically below the medical clip 10'''', the medical clip 10'''' of the present example makes it possible to easily grab the wound site without greatly rotating the endoscope 3 due to the structure of the first ancillary arm 110''' and the second ancillary arm 210''' bent by the predetermined angle (S). Thus, a turning radius for treatment by the endoscope 3 can be increased.

[Use of Clip Unit]

FIGS. 11a to 11e are provided to explain a use state of a clip unit to which the medical clip according to the preferred example of the present invention is applied.

Figure 11A:
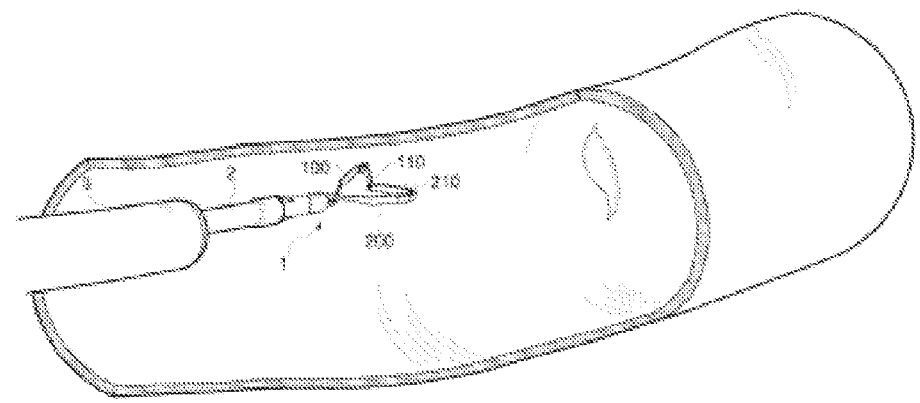
FIGS. 11a to 11e are use state diagrams of a clip unit to which a medical clip according to a preferred example of the present invention is applied.

As shown in FIG. 11a, a clip unit 1 is connected to the clip unit-controlling device 2 manipulated as being inserted into treatment instrument insertion channel of the endoscope 3, and is penetrated into the patient's organ. At this time, the first ancillary arm 110 and the second ancillary arm 210 are folded into the inner side of the first arm 100 and the second arm 200, respectively.

Figure 11B:
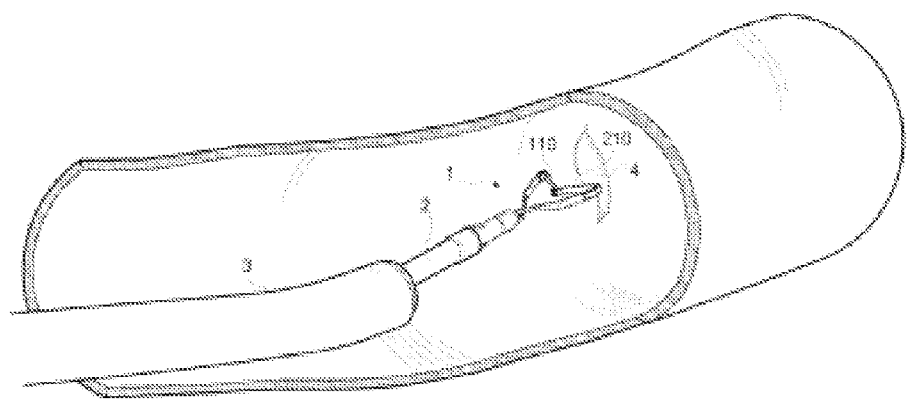

Further, as shown in FIG. 11b, the clip unit 1 is allowed to approach the vicinity of the site 4 to be treated in the organ by manipulating the endoscope 3. At this time, since the first ancillary arm 110 and the second ancillary arm 210 are still folded into the inner side of the first arm 100 and the second arm 200, respectively, it is easy to manipulate the endoscope 3 even in a small space.

Figure 11C:
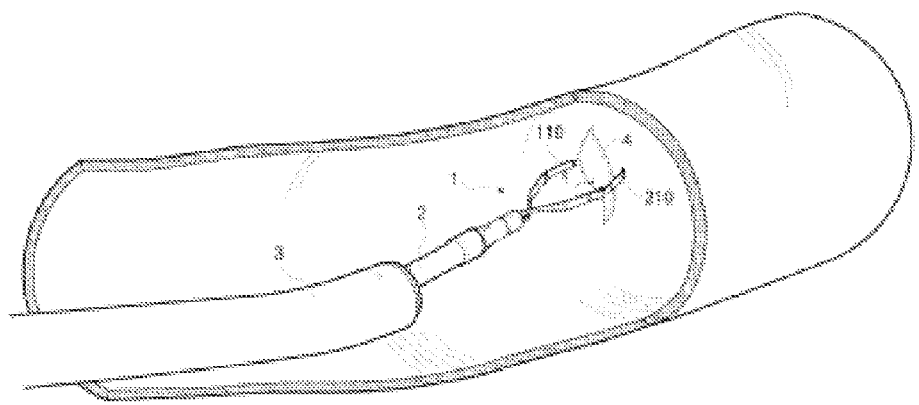

Furthermore, as shown in FIG. 11c, after the clip unit 1 is allowed to further approach a front surface of the site 4 to be treated, the first ancillary arm 110 and the second ancillary arm 210 are turned in an upstanding state, respectively, by manipulating the clip unit-controlling device 2. At this time, there is an effect as if the first arm 100 and the second arm 200 are extended as much as the first ancillary arm 110 and the second ancillary arm 210 are upstanding. Therefore, even if a width of the site 4 to be treated is large, the edge of the site 4 can be easily picked up.

Figure 11D:
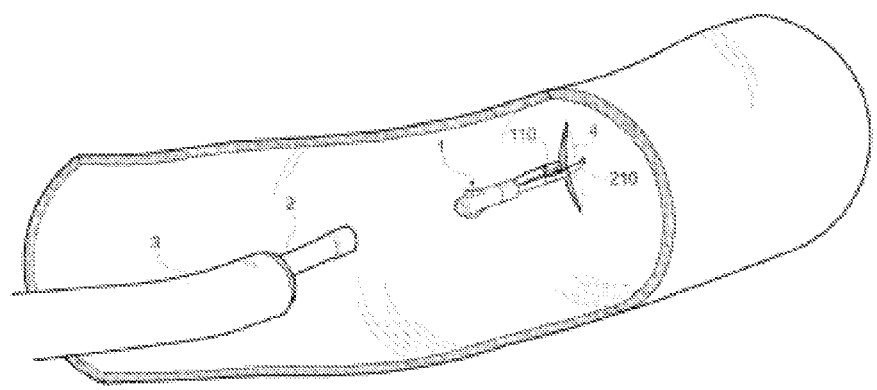

Further, as shown in FIG. 11d, while the first ancillary arm 110 and the second ancillary arm 210 pick up the edge of the site 4 to be treated by manipulating the clip unit-controlling device (not shown), the clip unit 1 is separated from the clip unit-controlling device 2.

Figure 11E:
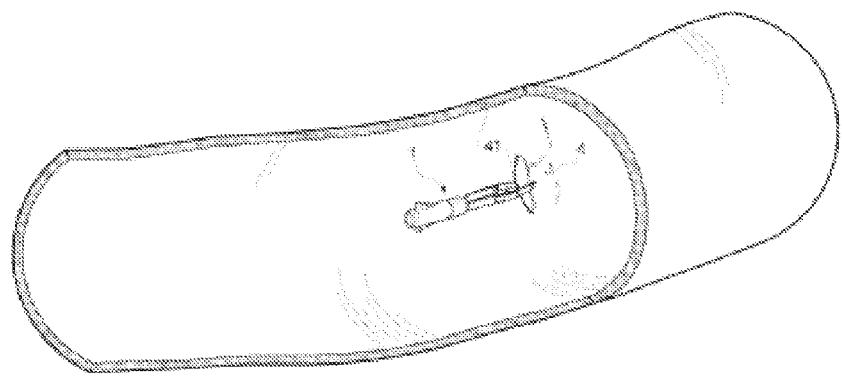

Furthermore, as shown in FIG. 11e, after a lapse of a certain time, the wound site 4 is normally sutured on the basis of the site being picked up by the first ancillary arm 110 and the second ancillary arm 210. Also, tissue 41 necrotized due to the picking-up by the first ancillary arm 110 and the second ancillary arm 210 is separated from the wound site 4 and then excreted from the body via defecation, etc., together with the clip unit 1.

INDUSTRIAL APPLICABILITY

The invention can be widely used as a medical instrument for endoscopic surgery or the like, and is not be limited to the use for human body and is also useful for animals. Further, it can be applied to the field that the endoscopic operation is required in a small space, as well as the medical instrument.

The invention claimed is:

1. A medical clip comprising:
   a first arm and a second arm between which a target is configured to be placed, wherein the first and second arms are configured to together squeeze the target;
   a ring configured to connect one end of the first arm with one end of the second arm;
   a first ancillary arm articulated with the other end of the first arm;
   a second ancillary arm articulated with the other end of the second arm;
   a first elastic member which is connected between the first arm and the first ancillary arm to provide power for spreading the first arm and the first ancillary arm from each other; and
   a second elastic member which is connected between the second arm and the second ancillary arm to provide power for spreading the second arm and the second ancillary arm from each other.

2. The medical clip of claim 1, wherein the first elastic member and the second elastic member are any one of elastic rubber and a torsion spring.

3. The medical clip of claim 1, wherein by at least one of a method using an adhesive, a heat-pressing method, a high-frequency attaching method, a photopolymerization method, and a bolt-fixing method, one end of the first elastic member and one end of the second elastic member are bonded to the first arm and the second arm, respectively, and the other end of the first elastic member and the other end of the second elastic member are bonded to the first ancillary arm and the second ancillary arm, respectively.

4. The medical clip of claim 1, wherein in the case where the first ancillary arm and the second ancillary arm are open, the first ancillary arm and the second ancillary arm are extended in directions dislocated to extension directions of the first arm and the second arm, respectively.

5. The medical clip of claim 1, wherein each of the first ancillary arm and the second ancillary arm includes multiple joints articulated with each other, and each of the joints is connected with an elastic member providing power for spreading the joints from each other.

6. The medical clip of claim 5, wherein each of the multiple joints is rolled and folded into an inner side between the first arm and the second arm.

7. The medical clip of claim 1, further comprising:
   a first fixing lock protruding from any one of the first arm and the first ancillary arm toward the other of them; and
   a second fixing lock protruding from any one of the second arm and the second ancillary arm toward the other of them.

8. The medical clip of claim 7, wherein a first inclined surface is formed on the first fixing lock and is configured to be in contact with the first arm, and a second inclined surface is formed on the second fixing lock and is configured to be in contact with the second arm.

9. A medical clip device comprising a medical clip unit comprising:
   a medical clip that includes a first arm and a second arm between which a target is configured to be placed and which is configured to together squeeze the target, a ring configured to connect one end of the first arm with one end of the second arm, a first ancillary arm articulated with the other end of the first arm, and a second ancillary arm articulated with the other end of the second arm;

a first elastic member which is connected between the first arm and the first ancillary arm to provide power for spreading the first arm and the first ancillary arm from each other; and a second elastic member which is connected between the second arm and the second ancillary arm to provide power for spreading the second arm and the second ancillary arm from each other:

a connecting member which is connected to the ring of the medical clip; and a pressing tube which is inserted in a state where the connecting member is connected with the ring.

10. The medical clip device of claim 9, comprising:

a wire which is connected with the connecting member of the medical clip; and a tubular body which is inserted into an endoscope and serves as a passage of the clip unit and the connecting member.

\* \* \* \* \*